United States Patent
Ishizawa et al.

(10) Patent No.: US 9,593,367 B2
(45) Date of Patent: Mar. 14, 2017

(54) GENETIC TEST SYSTEM

(75) Inventors: Masato Ishizawa, Tokyo (JP); Yoshiyuki Shoji, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 48 days.

(21) Appl. No.: 14/235,869

(22) PCT Filed: May 30, 2012

(86) PCT No.: PCT/JP2012/003514
§ 371 (c)(1),
(2), (4) Date: Jan. 29, 2014

(87) PCT Pub. No.: WO2013/018261
PCT Pub. Date: Feb. 7, 2013

(65) Prior Publication Data
US 2014/0193893 A1    Jul. 10, 2014

(30) Foreign Application Priority Data
Aug. 1, 2011 (JP) .................................. 2011-167975

(51) Int. Cl.
C12Q 1/68       (2006.01)
G01N 35/04     (2006.01)
G01N 35/00     (2006.01)

(52) U.S. Cl.
CPC ........... *C12Q 1/6844* (2013.01); *G01N 35/04* (2013.01); *G01N 2035/00346* (2013.01)

(58) Field of Classification Search
None
See application file for complete search history.

(56) References Cited

U.S. PATENT DOCUMENTS

| | | | | |
|---|---|---|---|---|
| 6,019,945 | A | * | 2/2000 | Ohishi ............... G01N 35/0092 422/63 |
| 2002/0016683 | A1 | * | 2/2002 | Shiba ............... G01N 35/00584 702/22 |
| 2005/0164375 | A1 | | 7/2005 | Inoue |

(Continued)

FOREIGN PATENT DOCUMENTS

| JP | 06-109745 A | 4/1994 |
|---|---|---|
| JP | 07-092171 A | 4/1995 |

(Continued)

*Primary Examiner* — Sean E Conley
*Assistant Examiner* — Benjamin Whatley
(74) *Attorney, Agent, or Firm* — Mattingly & Malur, PC

(57) ABSTRACT

There is provided a genetic test system provided with a dispensing means for dispensing a sample and a reagent to a reaction vessel and a vessel conveyance means for conveying the reaction vessel. The system further includes a plurality of nucleic acid amplification detection units, each including a temperature control means for accommodating a plurality of reaction vessels and performing temperature control for each accommodated position of the reaction vessel, a temperature monitoring means for monitoring a value of temperature to be controlled of the reaction vessel, and a light emission measurement means for measuring light emission of reaction liquid in the reaction vessel. At least one of the nucleic acid amplification detection units individually has a vessel conveyance means different from the above-mentioned vessel conveyance means.

7 Claims, 12 Drawing Sheets

SINGLE (ONE) ADDITIONAL
DEVICE IS ADDED AS COMPONENT

(56) References Cited

U.S. PATENT DOCUMENTS

| | | |
|---|---|---|
| 2006/0083660 A1 | 4/2006 | Schorno et al. |
| 2009/0221060 A1 | 9/2009 | Yamamoto et al. |
| 2009/0223308 A1 | 9/2009 | Fukuma |
| 2009/0305392 A1 | 12/2009 | Alfredsson et al. |
| 2010/0261184 A1 | 10/2010 | Park et al. |
| 2010/0284862 A1* | 11/2010 | Kakizaki ............ G01N 35/1004 422/82.05 |
| 2011/0104703 A1* | 5/2011 | Maeda ................. G01N 35/025 435/6.1 |
| 2011/0256532 A1* | 10/2011 | Sano ........................ C12Q 1/68 435/6.1 |
| 2011/0294131 A1* | 12/2011 | Maeda ................. G01N 35/025 435/6.12 |
| 2012/0207646 A1* | 8/2012 | Osaka ................. G01N 35/025 422/68.1 |
| 2013/0078712 A1* | 3/2013 | Sano .................... G01N 35/025 435/289.1 |
| 2013/0121881 A1* | 5/2013 | Ishizawa ............. G01N 35/026 422/82.08 |
| 2013/0130229 A1* | 5/2013 | Sugiyama ........... G01N 35/026 435/3 |
| 2013/0130369 A1* | 5/2013 | Wilson ................. B01L 3/5085 435/289.1 |
| 2013/0224753 A1* | 8/2013 | Ishizawa .......... G01N 35/00623 435/6.12 |

FOREIGN PATENT DOCUMENTS

| | | | | |
|---|---|---|---|---|
| JP | 09-224644 A | | 9/1997 | |
| JP | H09224644 A | * | 9/1997 | ............. C12M 1/00 |
| JP | 11-271324 A | | 10/1999 | |
| JP | 11-304812 A | | 11/1999 | |
| JP | 2000-088860 A | | 3/2000 | |
| JP | 2002-048802 A | | 2/2002 | |
| JP | 2005-233938 A | | 9/2005 | |
| JP | 2005-292138 A | | 10/2005 | |
| JP | 2006-115742 A | | 5/2006 | |
| JP | 2008-185389 A | | 8/2008 | |
| JP | 2008185389 A | * | 8/2008 | ............. G01N 35/00 |
| JP | 2008-278832 A | | 11/2008 | |
| JP | 2009-201444 A | | 9/2009 | |
| JP | 2009-216442 A | | 9/2009 | |
| JP | 2009-544955 A | | 12/2009 | |
| JP | 2010-051265 A | | 3/2010 | |
| JP | 2010-151665 A | | 7/2010 | |
| JP | 2010151665 A | * | 7/2010 | |
| JP | 2011-505130 A | | 2/2011 | |
| JP | 2011-234369 A | | 11/2011 | |
| JP | 2013-126421 A | | 6/2013 | |
| JP | 2013-14859 A | | 8/2013 | |
| WO | WO 2012063736 A1 | * | 5/2012 | ....... G01N 35/00623 |

* cited by examiner

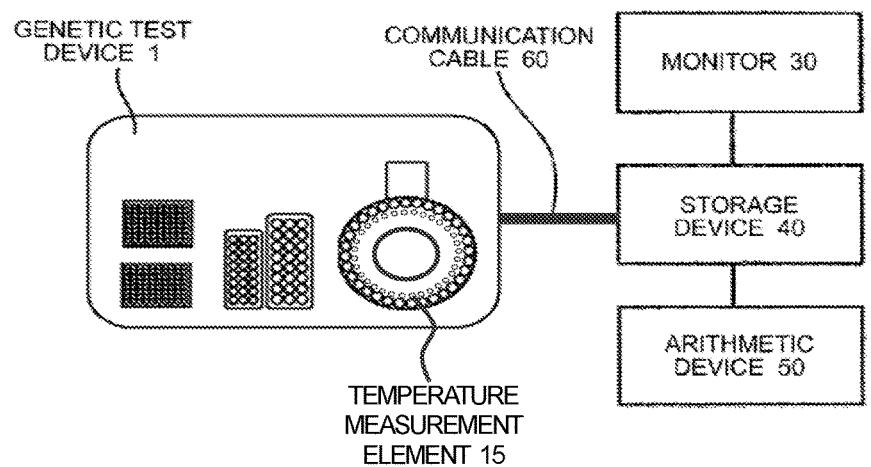
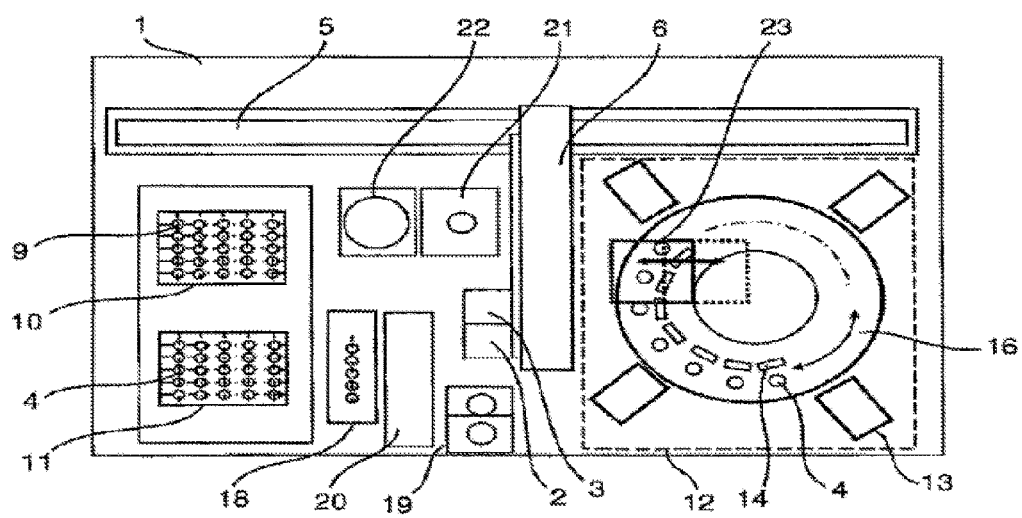

SINGLE (ONE) ADDITIONAL
DEVICE IS ADDED AS COMPONENT

PLURALITY OF (TWO) ADDITIONAL
DEVICES ARE ADDED AS COMPONENTS

PLURALITY OF (THREE) ADDITIONAL
DEVICES ARE ADDED AS COMPONENTS

IN EACH DEVICE, PLURALITY OF TYPES OF
DETECTORS CAN BE CONSTRUCTED, THAT IS,
PLURALITY OF COMBINATIONS OF
EXCITATION-WAVELENGTH AND
FLUORESCENCE-WAVELENGTH VALUES CAN
BE SELECTED

| | 1 DETECTORS IN GENETIC TEST DEVICE | | | 31a DETECTORS IN ADDITIONAL DEVICE | | | 31b DETECTORS IN ADDITIONAL DEVICE | |
|---|---|---|---|---|---|---|---|---|
| | 13a DETECTOR (FIRST) | 13b DETECTOR (SECOND) | | 13c DETECTOR (FIRST) | 13d DETECTOR (SECOND) | | 13e DETECTOR (FIRST) | 13f DETECTOR (SECOND) |
| EXCITATION WAVELENGTH (nm) | 465 | 465 | | 465 | 465 | | 465 | 465 |
| FLUORESCENCE WAVELENGTH (nm) | 517 | 517 | | 517 | 517 | | 517 | 517 |

ONLY ONE COMBINATION EXISTS IN SYSTEM, AND ALL DETECTORS HAVE SAME COMBINATION

| | 1 DETECTORS IN GENETIC TEST DEVICE | | | 31a DETECTORS IN ADDITIONAL DEVICE | | | 31b DETECTORS IN ADDITIONAL DEVICE | |
|---|---|---|---|---|---|---|---|---|
| | 13a DETECTOR (FIRST) | 13b DETECTOR (SECOND) | | 13c DETECTOR (FIRST) | 13d DETECTOR (SECOND) | | 13e DETECTOR (FIRST) | 13f DETECTOR (SECOND) |
| EXCITATION WAVELENGTH (nm) | 465 | 550 | | 465 | 550 | | 550 | 465 |
| FLUORESCENCE WAVELENGTH (nm) | 517 | 595 | | 517 | 595 | | 595 | 517 |

PLURALITY OF TYPES OF COMBINATIONS EXIST IN SYSTEM, AND SET OF COMBINATIONS IS SAME IN EACH DEVICE

FIG. 10

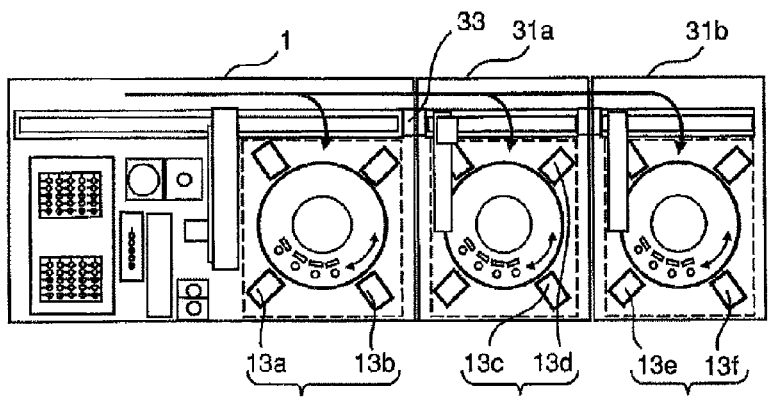

| | 1 DETECTORS IN GENETIC TEST DEVICE | | | 31a DETECTORS IN ADDITIONAL DEVICE | | | 31b DETECTORS IN ADDITIONAL DEVICE | |
|---|---|---|---|---|---|---|---|---|
| | 13a DETECTOR (FIRST) | 13b DETECTOR (SECOND) | | 13c DETECTOR (FIRST) | 13d DETECTOR (SECOND) | | 13e DETECTOR (FIRST) | 13f DETECTOR (SECOND) |
| EXCITATION WAVELENGTH (nm) | 465 | 550 | | 640 | 365 | | 495 | 380 |
| FLUORESCENCE WAVELENGTH (nm) | 517 | 595 | | 475 | 517 | | 515 | 525 |

PLURALITY OF TYPES OF COMBINATIONS EXIST IN SYSTEM, AND ALL DETECTORS HAVE DIFFERENT COMBINATIONS FROM ONE ANOTHER

| | 1 DETECTORS IN GENETIC TEST DEVICE | | 31a DETECTORS IN ADDITIONAL DEVICE | | 31b DETECTORS IN ADDITIONAL DEVICE | |
|---|---|---|---|---|---|---|
| | 13a DETECTOR (FIRST) | 13b DETECTOR (SECOND) | 13c DETECTOR (FIRST) | 13d DETECTOR (SECOND) | 13e DETECTOR (FIRST) | 13f DETECTOR (SECOND) |
| MEASUREMENT ITEM | HBV | HBV | HCV | HCV | HPV | HPV |

PLURALITY OF TYPES OF MEASUREMENT ITEMS EXIST IN SYSTEM, AND DETECTORS OF EACH DEVICE HAS SAME MEASUREMENT ITEM

FIG. 13

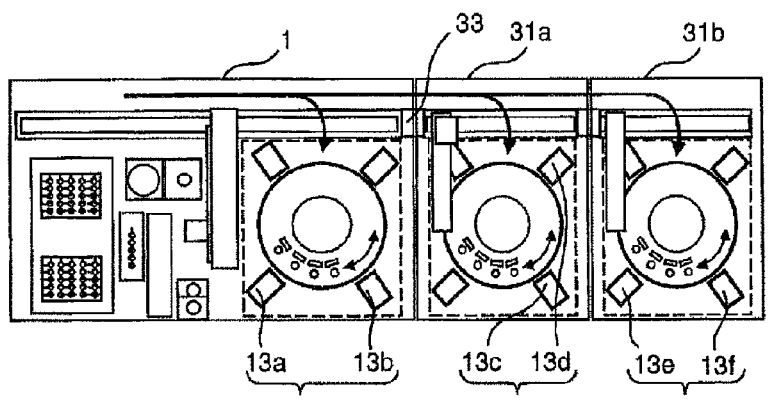

| | 1 DETECTORS IN GENETIC TEST DEVICE | | | 31a DETECTORS IN ADDITIONAL DEVICE | | | 31b DETECTORS IN ADDITIONAL DEVICE | |
|---|---|---|---|---|---|---|---|---|
| | 13a DETECTOR (FIRST) | 13b DETECTOR (SECOND) | | 13c DETECTOR (FIRST) | 13d DETECTOR (SECOND) | | 13e DETECTOR (FIRST) | 13f DETECTOR (SECOND) |
| MEASUREMENT ITEM | HBV | HCV | | HBV | HCV | | HBV | HCV |

PLURALITY OF TYPES OF MEASUREMENT ITEMS EXIST IN SYSTEM, AND COMBINATION OF MEASUREMENT ITEMS IS SAME IN EACH DEVICE

PLURALITY OF TYPES OF MEASUREMENT ITEMS EXIST IN SYSTEM, AND ALL DETECTORS HAVE DIFFERENT MEASUREMENT ITEMS FROM ONE ANOTHER

SINGLE (ONE) PREPROCESSING EXTRACTION DEVICE IS ADDED AS COMPONENT

PLURALITY OF (TWO) PREPROCESSING EXTRACTION
DEVICE ARE ADDED AS COMPONENTS

| SPECIMEN INLET 1 | SPECIMEN INLET 2 | SPECIMEN INLET 3 | SPECIMEN INLET 4 |

TEMPERATURE CONTROL MEANS CONVEYS REACTION VESSEL BETWEEN PLURALITY
OF TEMPERATURE BATHS EACH IN WHICH SPECIFIC TEMPERATURE IS SET

GENETIC TEST SYSTEM

TECHNICAL FIELD

The present invention relates to an analysis method and apparatus for qualitatively or quantitatively analyzing a target nucleic acid contained in a biological sample such as blood and urine and includes a technology that requires a temperature change in reaction liquid amplification and detection processes and a technique that does not require a temperature change in reaction liquid amplification and detection processes.

BACKGROUND ART

Nucleic acid amplification technologies, such as a polymerase chain reaction (hereinafter, referred to as "PCR") that requires a temperature change in reaction liquid amplification and detection processes and a loop mediated isothermal amplification method (hereinafter, referred to as "LAMP method") that does not require a temperature change in reaction liquid amplification and detection processes, have been used for amplification and quantification of nucleic acids contained in samples originating in living organisms. For nucleic acid amplification, PCR requires periodically changing a sample temperature in typically about two to three temperature regions. For example, a typical PCR is performed as follows: the sample temperature is heated up to 94° C. to separate the double strands, followed by annealing at 60° C., and the sample temperature is kept at 60° C. to 72° C. for a few minutes. This PCR process is repeated by n times to amplify a target nuclear acid. On the other hand, in the LAMP method, reaction proceeds at a constant temperature of 60° C. to 65° C. As described above, amplification is made within a certain constant temperature range as described above in the LAMP method. However, since it is important to control temperatures of a plurality of reaction vessels, the present invention can be applied to the LAMP method. Further, an amplification temperature may differ depending on a sample to be used.

In order to realize such a periodic temperature control method in PCR, PTL 1 listed below discloses a device that includes regions maintained at different set temperatures and a disc-shaped sample holder, wherein the sample temperature is periodically changed by rotation of the disc.

However, in the PCR, the temperature and time required for the annealing reaction of binding primers to their complementary sequences in the detection target base sequences differ depending on the sequences. The temperature and time required for extension reaction also differ depending on a type of an enzyme to be added. Thus, if the detection target base sequences, specifically a plurality of reaction liquids of different protocols are to be simultaneously processed, a nucleic acid amplification device having settings for the temperature and time specified by the protocol is needed in the same number as the number of the protocols to be simultaneously processed.

There is known a technology that includes a plate for holding a plurality of samples and that evenly controls temperature over the whole plate. However, the PCR involves a temperature cycle consisting of denaturation reaction, annealing reaction, and extension reaction, and an analysis is finished after repeating a certain number of cycles. In the technology to evenly control temperature over the whole plate, an analysis of a new sample cannot be started once an analysis of a sample is started and until the analysis ends, even when the protocols are the same. This is problematic, because obtaining an analysis result for the new sample takes a long time.

Further, as described above, this technology is operated in a batch mode in a device that includes a plate for holding a plurality of samples and that evenly controls temperature over the whole plate, so that a temperature locality disadvantageously appears in the plate.

CITATION LIST

Patent Literature

PTL 1: JP 2008-185389 A
PTL 2: JP 09-224644 A
PTL 3: JP 2006-115742 A

SUMMARY OF INVENTION

Technical Problem

Typically, a time required for reaction in a genetic test analysis method is evidently longer than that in a measurement method for biochemical analysis or immunological analysis. Thus, a specimen to be measured stays for a long time in a test device, which is a main factor that makes it difficult to enhance throughput of the device and leads to an increase in size of the device.

An object of the present invention is to provide a system configuration capable of easily enhancing throughput and function of a genetic test device.

Solution to Problem

According to the present invention, a genetic test device includes a heating/cooling means for accommodating a plurality of reaction vessels accommodating as target nucleic acid to be amplified and a component required for the amplification and performing temperature control for each accommodated position of the reaction vessel, a temperature monitoring means for monitoring a value of temperature to be controlled of the reaction vessel, and a light emission detection means for measuring light emission of reaction liquid in the reaction vessel. This genetic test device is connected with an additional device including the heating/cooling means, the temperature monitoring means, and the light emission detection means which are partial constituent elements of the above genetic test device and further connected with a preprocessing extraction device of DNA/RNA for functional extension to thereby construct a functionally extended system. This allows a genetic test system with high added value to be provided.

Advantageous Effects of Invention

According to the present invention, it is possible to easily realize functional enhancement and functional extension for achievement of, e.g., high throughput and contribute to an increase in quality of analysis data. Further, a fail-safe function for backup at a trouble time can be easily realized in the functionally extended system, thereby allowing a device with very high added value for customers and a genetic test system having high reliability to be provided.

BRIEF DESCRIPTION OF DRAWINGS

FIG. 1 is an entire configuration view of a genetic test device according to an embodiment of the present invention.

FIG. 2 is an internal configuration view of the genetic test device according to the present embodiment.

FIG. 10 is a configuration view illustrating an application example of a combination of detectors in the genetic test system according to the present embodiment.

FIG. 13 is a configuration view illustrating an application example of a combination of measurement items in the genetic test system according to the present embodiment.

DESCRIPTION OF EMBODIMENTS

Figure 3:
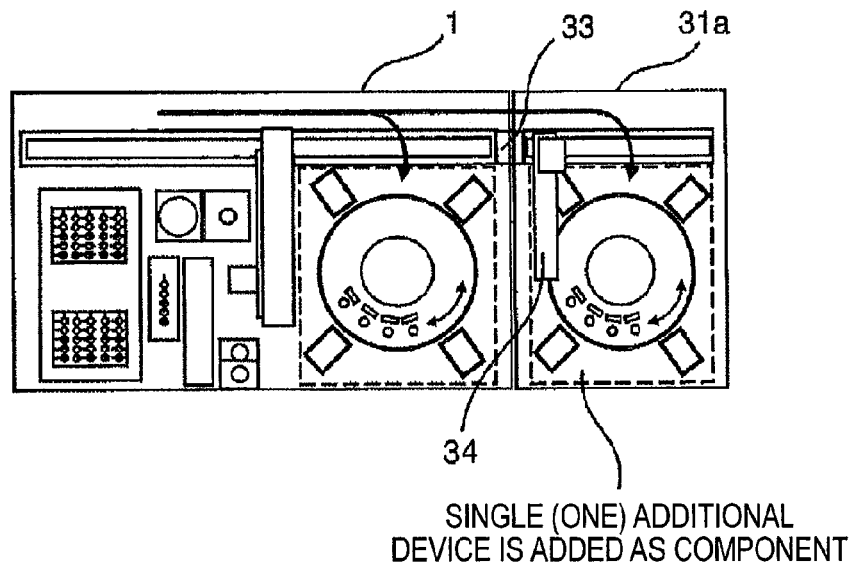
FIG. 3 is a system configuration view of the genetic test system according to the present embodiment.

The present invention relates to a system configuration for realizing functional extension and functional enhancement of a genetic test device having a temperature control mechanism for performing nucleic acid amplification by a PCR reaction and capable of changing temperature in a plurality of individual vessel installation units and a plurality of detectors that irradiate reaction liquid with excitation light to perform light emission detection such as fluorescence detection.

A system configuration in which an additional device including a temperature control mechanism and a detector can be easily connected to a fundamental genetic test device allows a genetic test device with high throughput and high reliability to be easily provided. Further, easy connection of a preprocessing extraction device that performs extraction of DNA/RNA allows a further functionally enhanced full-automatic genetic test device having higher reliability to be provided.

An object of the present invention is to provide a system configuration capable of easily enhancing throughput and function of a genetic test device. Typically, a time required for reaction in a genetic test analysis method is evidently longer than that in a measurement method for biochemical analysis or immunological analysis. Thus, a specimen to be measured stays for a long time in a test device, which is a main factor that makes it difficult to enhance throughput of the device and leads to an increase in size of the device.

According to the present invention, a genetic test device includes a heating/cooling means for accommodating a plurality of reaction vessels accommodating as target nucleic acid to be amplified and a component required for the amplification and performing temperature control for each accommodated position of the reaction vessel, a temperature monitoring means for monitoring a value of temperature to be controlled of the reaction vessel, and a light emission detection means for measuring light emission of reaction liquid in the reaction vessel. This genetic test device is connected with an additional device including the heating/cooling means, the temperature monitoring means, and the light emission detection means which are partial constituent elements of the above genetic test device and further connected with a preprocessing extraction device of DNA/RNA to thereby construct a functionally extended system. This allows a genetic test system with high added value to be provided.

According to the present invention, it is possible to easily realize functional enhancement and functional extension for achievement of, e.g., high throughput and contribute to an increase in quality of analysis data. Further, a fail-safe function for backup at a trouble time can be easily realized in the functionally extended system, thereby allowing a device with very high added value for customers and a genetic test system having high reliability to be provided.

FIG. 1 is a schematic view of an entire configuration of a nucleic acid analysis device embodying the present invention. A genetic test device 1 is connected to a monitor 30, a storage device 40, and an arithmetic device 50 through a communication cable 60. The monitor serves as an operation section for controlling the genetic test device 1.

FIG. 2 is a view illustrating an internal configuration of the genetic test device 1. With reference to FIG. 2, constituting elements of major mechanisms will be described. A dispensing unit 2 is provided for suction and ejection of liquid. A gripper unit 3 holds a reaction vessel 4. The dispensing unit 2 and gripper unit 3 are each connected to a robot arm X axis 5 and a robot arm Y axis 6 so as to be movable in a plane to thereby move the held reaction vessel according to a predetermined procedure.

Dispensing tips 9 are stored in a nozzle tip rack 10. The dispensing tips 9 are made disposable for prevention of contamination. The reaction vessel 4 is a vessel to which a sample and a reagent are ejected and is stored in a reaction vessel rack 11.

A nucleic acid amplification unit 12 according to the embodiment of the present invention is constituted by a rotatable disk with a plurality of thermostat baths 16 and a plurality of detectors 13 arranged around the thermostat baths 16. More than one thermostat baths 16 are provided to accommodate a plurality of reaction vessels 4, and the reaction vessels are provided in a one-to-one relationship with the thermostat baths 16. With this configuration, the individual reaction vessels 4 can be controlled/monitored in terms of temperature.

A representative operation process of the genetic test device 1 is initiated by conveying the reaction vessel 4 to a reaction liquid adjustment position 18 using the gripper unit 3.

With the dispensing tip 9 attached to the dispensing unit 2, a sample and a reagent are sucked from sample and reagent vessels 19, respectively, and ejected into the reaction vessel 4 at the reaction liquid adjustment position 18. The reagent is also ejected into the reaction vessel 4 in the same procedure. The dispensing tip 9 after use is discarded in a waste box 20 to prevent contamination.

After the sample and reagent ejection, the reaction vessel 4 is sealed by being capped with a closing unit 21 and agitated with an agitation unit 22. The reaction vessel 4 is then carried in to the nucleic acid amplification unit 12, and detection is performed with the detector 13. After completion of the detection process, the reaction vessel 4 is discarded in the waste box 20 by the gripper unit 3. The carry-in and carry-out of the reaction vessel 4 to and from the nucleic acid amplification unit 12 are performed by opening and closing a gate 23.

According to the present embodiment, the temperature of each thermostat bath is increased or decreased by an electrothermal element 14 and is always monitored by a pole temperature measurement element to thereby execute a predetermined temperature profile. This allows prevention of unnecessary locality of a temperature distribution even when a method like the PCR in which a plurality of temperatures need to be managed is employed, thereby allowing easy automation of a quantification process of the amplified nucleic acids.

FIG. 3 is a configuration example of a genetic test system obtained by connecting, for functional extension, an additional device 31a to the genetic test device 1 according to the embodiment of the present invention. Although one extension device 31a is provided for one genetic test device 1 in the example of FIG. 3, two extension devices 31a and 31b (FIG. 4) or three extension devices 31a, 31b, and 31c (FIG. 5) may be connected to one genetic test device 1 for further functional extension.

Figure 4:
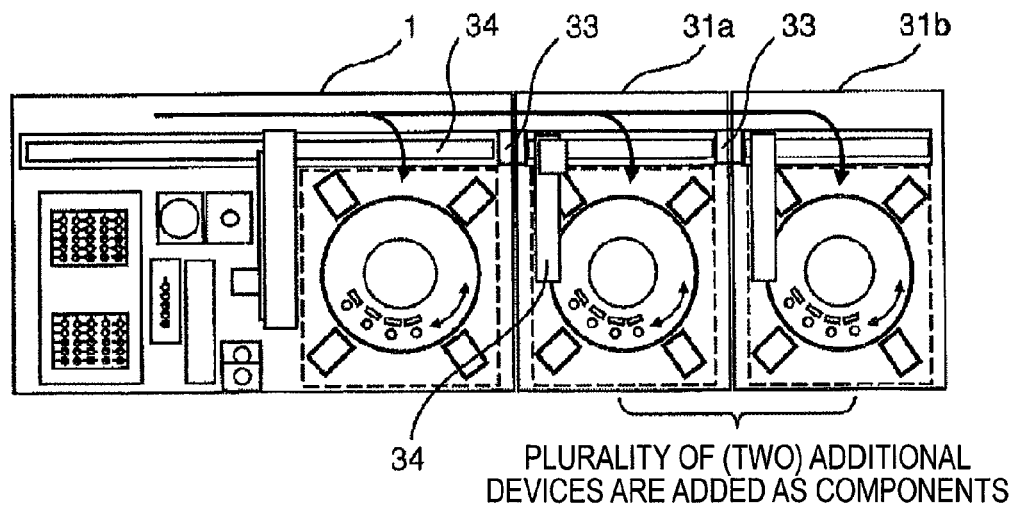
FIG. 4 is a system configuration view of the genetic test system according to the present embodiment.
Figure 5:
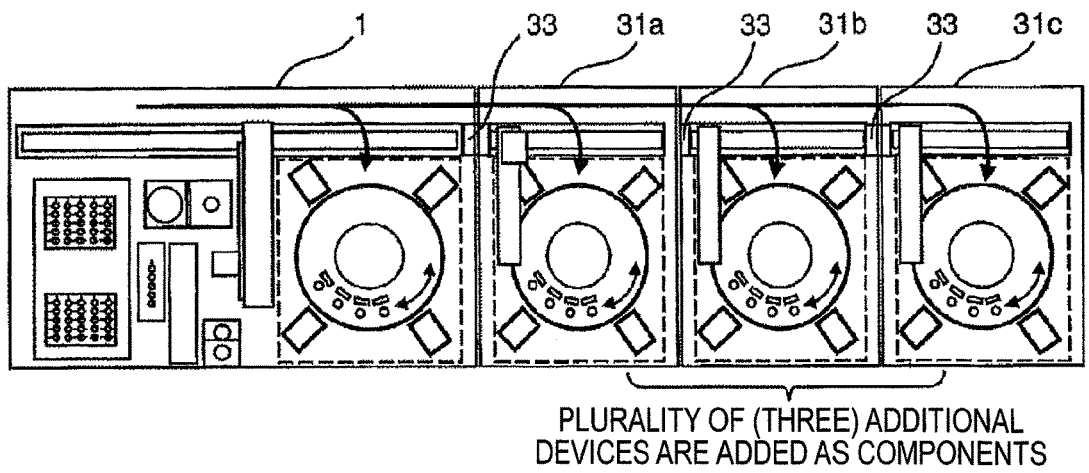
FIG. 5 is a system configuration view of the genetic test system according to the present embodiment.
Figure 6:
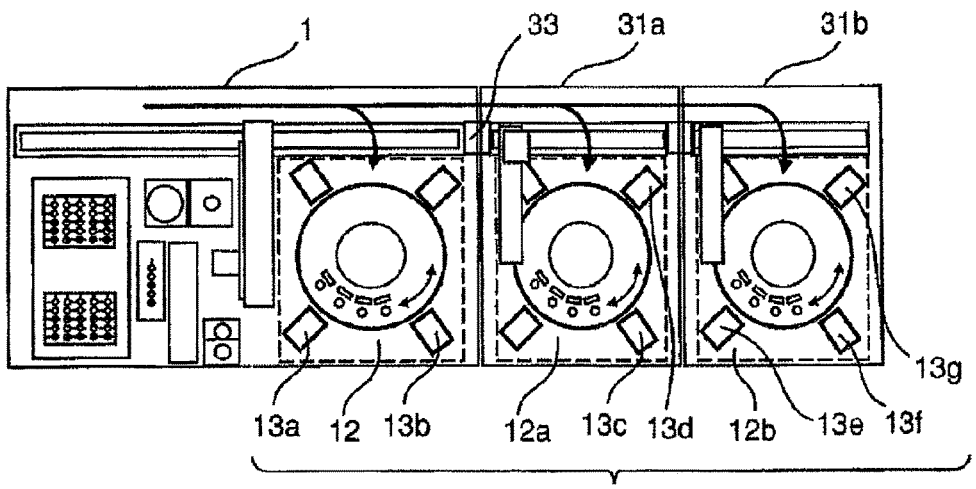
FIG. 6 is a view illustrating a basic feature of the genetic test system according to the present embodiment.

The function to be extended by the system configurations illustrated in FIGS. 3 to 5 is throughput. Typically, the time required for reaction in the genetic test analysis method is about one hour to two hours, which is defined by an assay protocol. Accordingly, the reaction vessel 4 stays in the thermostat bath 16 for a time defined by the above assay protocol, which is a main factor that makes it difficult to enhance throughput of the device.

The additional device 31 devised by the present invention includes therein the nucleic acid amplification unit 12 and a gripper arm 34. With this additional device 31, it is possible to easily extend the thermostat bath 16, that is, it is possible to easily double the throughput.

The conveyance of the reaction vessel 4 between the genetic test device 1 and additional device 3 is made by means of an extension means 33. A thick arrow in FIGS. 3 to 5 and FIGS. 6 to 18 represents a flow of the specimen to be analyzed in the system. As illustrated in FIG. 5, in the system, a device that analyzes the specimen can be identified. Specifically, in the system, it is possible to control to which one of the genetic test device 1 and additional devices 31a to 31c the specimen is carried in for analysis.

That is, it is possible to easily perform intelligence conveyance control of the specimen so as to achieve optimum performance (e.g., an increase in availability of the entire system) by controlling a conveyance destination of the specimen according to the internal configurations or device statuses of the genetic test device 1 and additional devices 31a to 31c.

The following describes more concrete cases to which the present invention is applied and additional values obtained therefrom with reference to FIGS. 6 to 18. A system illustrated in FIG. 6 having a configuration like that of FIG. 4, in which two additional devices 31a and 31b are added, includes four detectors in each of the nucleic acid amplification units 12, 12a, and 12b, that is, includes 12 detectors in total and can set therein different excitation wavelength values and fluorescence wavelength values from one another. That is, a detector having 12 combinations of the excitation-wavelength value and fluorescence-wavelength value can be constructed in one system.

Further, a plurality of detectors having a combination of a specific excitation-wavelength value and fluorescence-wavelength value can be constructed in one system. Thus, a system having very high redundancy can be constructed.

In the above example, four detectors are provided for each device in the above example; however, the number of detectors to be provided is a value naturally resulting from a physical dimension of the entire device to which the detector is mounted or a geometric dimension of the detector itself, and the present invention does not define an upper limit of the number of detectors to be provided.

Figure 7:
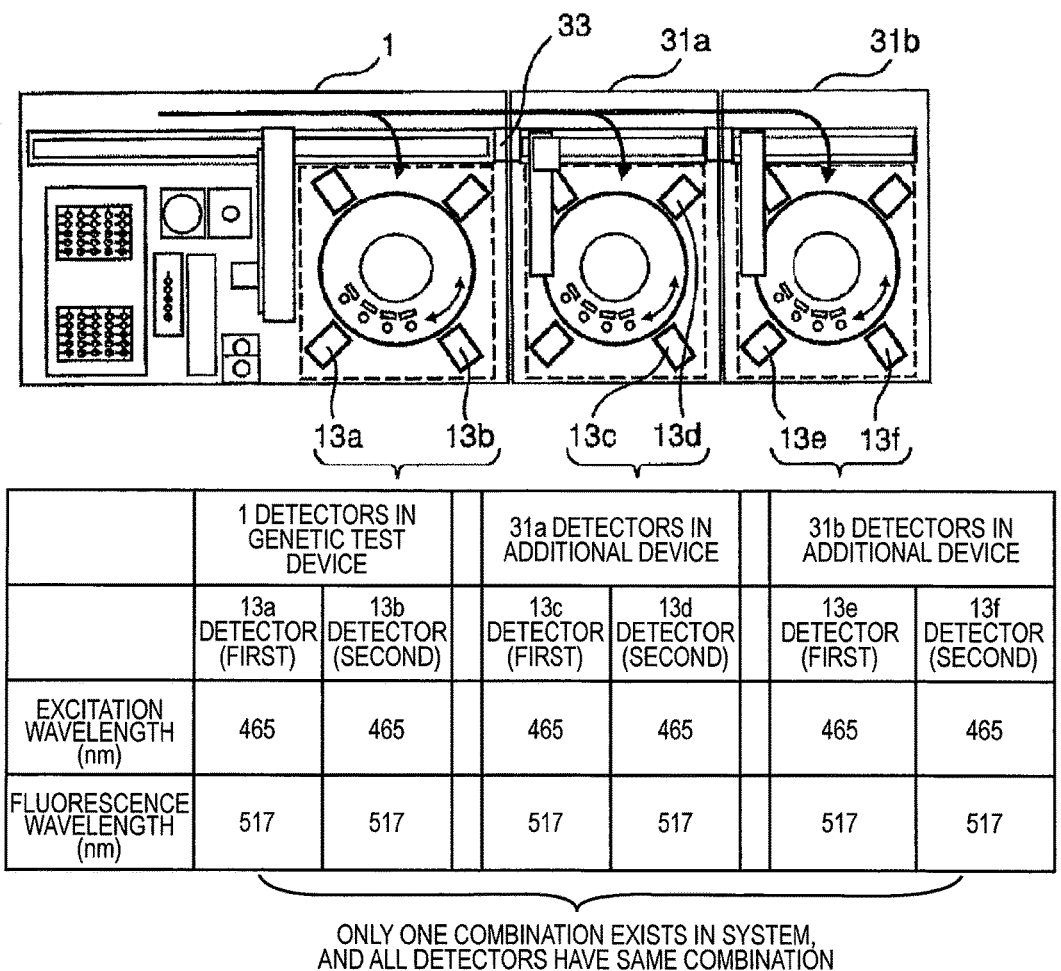
FIG. 7 is a configuration view illustrating an application example of a combination of detectors in the genetic test system according to the present embodiment.

FIGS. 7 to 14 each illustrate an example of a combination of the excitation-wavelength value and fluorescence-wavelength value in a configuration in which the additional devices 31a and 31b are connected to the genetic test device 1. FIG. 7 illustrates an example of a system configuration in which all the six detectors 13a to 13f provided in the genetic test device 1, additional device 31a, and additional device 31b have the same combination of the excitation-wavelength value and fluorescence-wavelength value. The system of this example can easily realize high throughput for the same assay protocol and is suitably used for, e.g., a case where a single test item is carried out for a large amount of specimen.

Figure 8:
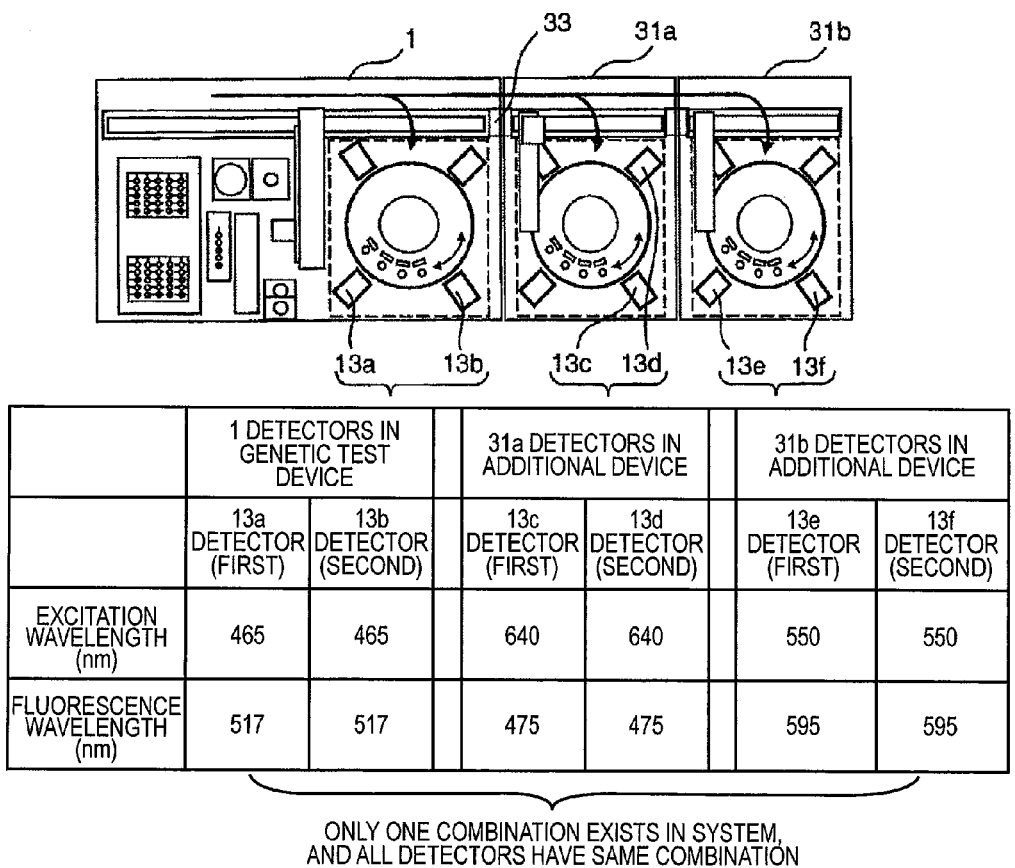
FIG. 8 is a configuration view illustrating an application example of a combination of detectors in the genetic test system according to the present embodiment.

FIG. 8 illustrates an example of a system configuration in which, as to the six detectors 13a to 13f, a combination of the excitation-wavelength value and fluorescence-wavelength value is made the same in each of the genetic test device 1, additional device 31a, and additional device 31b, but is made different among the three devices. In the case of this system configuration, a measurement device is specified for each assay protocol, and when another test needs to be performed for a specific specimen, measurement is made in the same device as that used previously. Further, by specifying the detector as that used in the previous measurement, it is possible to provide a measurement result having high reproducibility.

Figure 9:
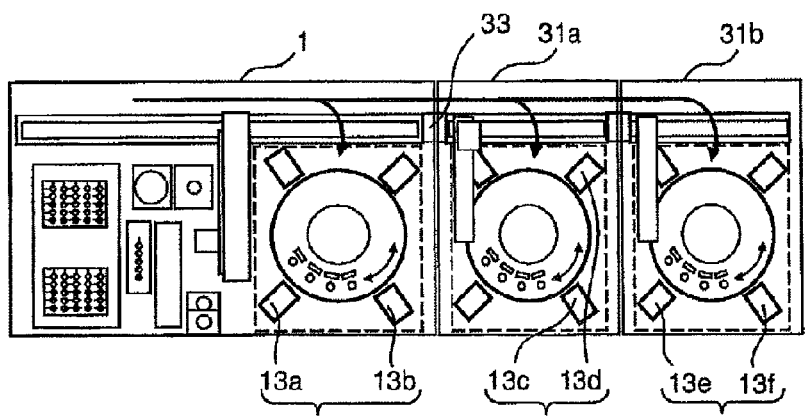
FIG. 9 is a configuration view illustrating an application example of a combination of detectors in the genetic test system according to the present embodiment.

In a system configuration illustrated in FIG. 9, as to the six detectors 13a to 13f, a combination of the excitation-wavelength value and fluorescence-wavelength value is made different in each of the genetic test device 1, additional device 31a, and additional device 31b, but a set of the combinations thereof is made the same among the three devices. In this configuration, a plurality of types of assay protocols can be measured in one device, and the same combination of the assay protocols can be measured among a plurality of devices.

Therefore, when a combination of assay protocols measured in a routine manner is previously obvious, high working efficiency can be achieved.

In a system configuration illustrated in FIG. 10, as to the six detectors 13a to 13f, a combination of the excitation-wavelength value and fluorescence-wavelength value is made different in each of the genetic test device 1, additional device 31a, and additional device 31b. Further, the combination of the excitation-wavelength value and fluorescence-wavelength value is made different among the three devices. That is, the detectors 13a to 13f have different combinations of the excitation-wavelength value and fluorescence-wavelength value. In this system configuration, a plurality of types of assay protocols can be measured in each device, and multiple analyses can be easily achieved in a single system, whereby significant improvement in operator workflow can be expected.

Figure 11:
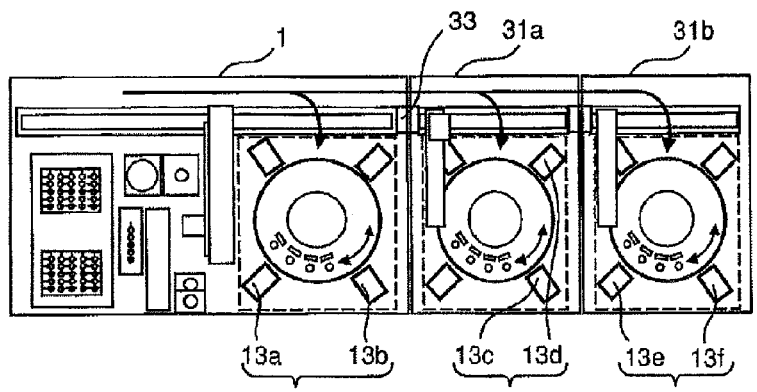
FIG. 11 is a configuration view illustrating an application example of a combination of measurement items in the genetic test system according to the present embodiment.

FIG. 11 illustrates an example of a system configuration represented in an image closer to reality, in which the combination of the excitation-wavelength value and fluorescence-wavelength value of the detectors 13a to 13f described in FIG. 7 is replaced with the measurement item of the specimen. As illustrated in FIG. 11, in this system configuration, the same measurement item is assigned to the detectors of the genetic test device 1, additional device 31a, and additional device 31b. In other words, this system configuration is suitable for realizing high throughput in single-item analysis. More specifically, this system configuration can satisfy requirements of customers, such as specified disease hospitals and testing centers, for measurement of a large number of specific analysis items.

Figure 12:
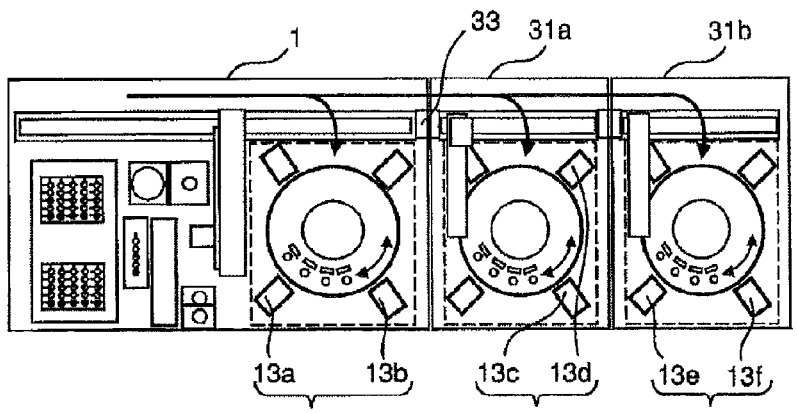
FIG. 12 is a configuration view illustrating an application example of a combination of measurement items in the genetic test system according to the present embodiment.

Similarly, FIG. 12 illustrates an example of a system configuration represented in an image closer to reality, in which the combination of the excitation-wavelength value and fluorescence-wavelength value of the detectors 13a to 13f described in FIG. 8 is replaced with the measurement item of the specimen. As illustrated in FIG. 12, in this system configuration, the measurement item which is the same in each of the genetic test device 1, additional device 31a, and additional device 31b but different among the devices is assigned to the detectors.

In other words, when a specific item is analyzed, the analyzing device is specified and, thus a variation in analysis results/analysis accuracy remains confined to the specified device, thereby increasing data reproducibility. More specifically, this system configuration can satisfy requirements of customers, such as specified disease hospitals, who performs analysis in which the measurement item is obvious and requires high reproducibility in the analysis results.

Similarly, FIG. 13 illustrates an example of a system configuration represented in an image closer to reality, in which the combination of the excitation-wavelength value and fluorescence-wavelength value of the detectors 13a to 13f described in FIG. 9 is replaced with the measurement item of the specimen. As illustrated in FIG. 13, in this system configuration, different measurement items are set in each of the genetic test device 1, additional device 31a, and additional device 31b, but the same combination of the measurement items is assigned to the detector pair in each of the devices. In other words, this system configuration is suitable for a workflow that processes a large number of combinations of specific analysis items. More specifically, this system configuration can be used for follow-up of inpatients in which items to be measured in a routine manner are obvious. In this case, by fixing a measurement device of a specimen to be measured in a routine manner, it is possible to increase reproducibility of analysis results, significantly contributing to an increase in quality of analysis data.

Figure 14:
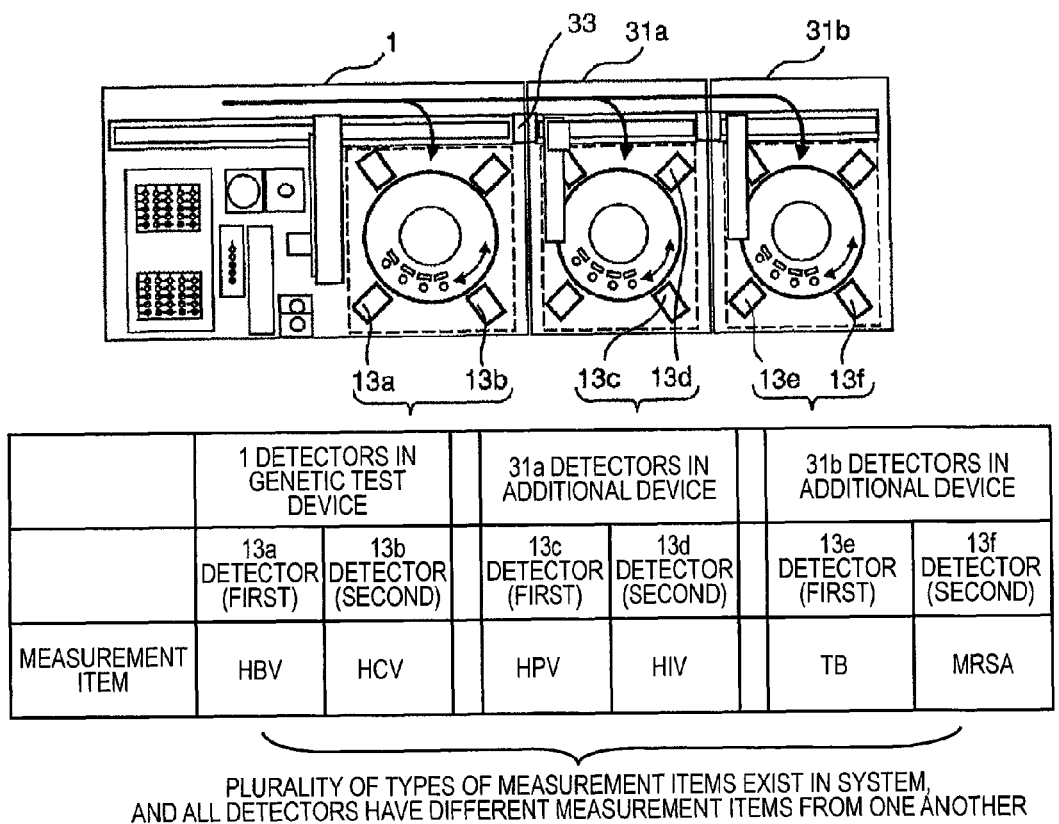
FIG. 14 is a configuration view illustrating an application example of a combination of measurement items in the genetic test system according to the present embodiment.

Similarly, FIG. 14 illustrates an example of a system configuration represented in an image closer to reality, in which the combination of the excitation-wavelength value and fluorescence-wavelength value of the detectors 13a to 13f described in FIG. 10 is replaced with the measurement item of the specimen. As illustrated in FIG. 14, in this system configuration, different measurement items are set in each of the genetic test device 1, additional device 31a, and additional device 31b and, further, all the detectors have different measurement items. In other words, this system configuration is suitable for realizing high throughput in single-item analysis.

More specifically, this system configuration is suitable for a workflow to be employed in a general hospital that mainly cares for outpatients, in which the measurement item and the number of items to be measured are not previously specified, measurement is performed on a wide variety of items, and there is a moderate amount of specimens for each measurement item.

Figure 15:
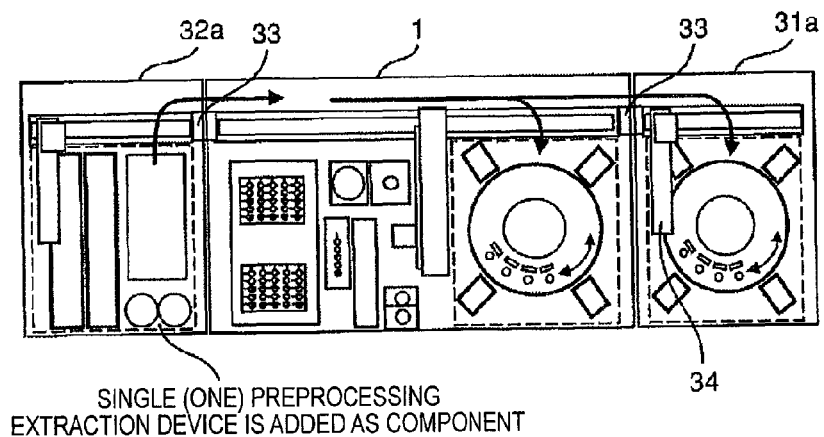
FIG. 15 is an extended system view illustrating a configuration in which a preprocessing extraction device for the genetic test system according to the present embodiment is connected thereto.

FIG. 15 illustrates an example of a configuration of a genetic test system in which the additional device 31a is connected to the genetic test device 1 according to the embodiment of the present invention and a nucleic acid extraction device 32a that automates extraction of DNA/RNA from a specimen to be measured is connected to an upstream side of the genetic test device 1 for full automation. The conveyance of the reaction vessel 4 between the nucleic acid extraction device 32a and genetic test device 1 is made by means of the extension means 33.

Figure 16:
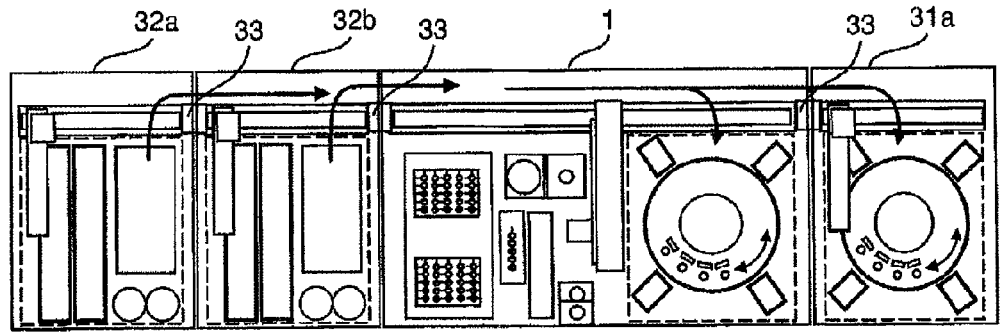
FIG. 16 is an extended system view illustrating a configuration in which a preprocessing extraction device for the genetic test system according to the present embodiment is connected thereto.

FIG. 16 illustrates a case where the function of the system configuration example of FIG. 15 is further extended. Specifically, two nucleic acid extraction devices 32a and 32b and two additional devices 31a and 31b are added for responding to higher functionality or further multifunctionality. Typically, it is obvious that an extraction process of DNA/RNA differs for each measurement item to make it very difficult to automate the process. Thus, allowing the plurality of nucleic acid extraction devices 32a and 32b to be incorporated in the system as illustrated in FIG. 16 enhances utility of the genetic test system as the fully automated system. In the example of FIG. 16, two nucleic acid extraction devices 32a and 32b are added; however, the number of the nucleic acid extraction devices to be added is a value naturally resulting from a physical dimension of the entire device, and the present invention does not define an upper limit of the number of the nucleic acid extraction devices to be added.

Figure 17:
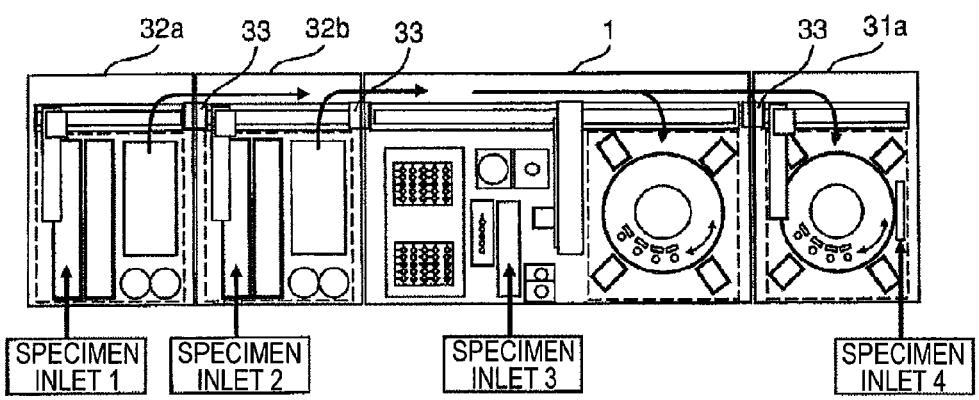
FIG. 17 is a view illustrating a layout of a specimen inlet in the genetic test system according to the present embodiment.

FIG. 17 is a view particularly illustrating a layout of an inlet of the specimen to be measured in the system configuration example of FIG. 16. A specimen inlet 1 and a specimen inlet 2 provided in the nucleic acid extraction devices 32a and 32b, respectively, are each a specimen inlet before DNA/RNA extraction. A specimen inlet 3 provided in the genetic test device 1 functions as a specimen inlet after DNA/RNA extraction. Further, the specimen inlet 3 functions also as an inlet for retesting of a specimen after DNA/RNA extraction. A specimen inlet 4 is a specimen inlet that can support a special use purpose such as execution of fluorescence measurement in the nucleic acid amplification unit 12 provided in the additional device 31a as an additional cycle after execution of a predetermined number of cycles.

Figure 18:
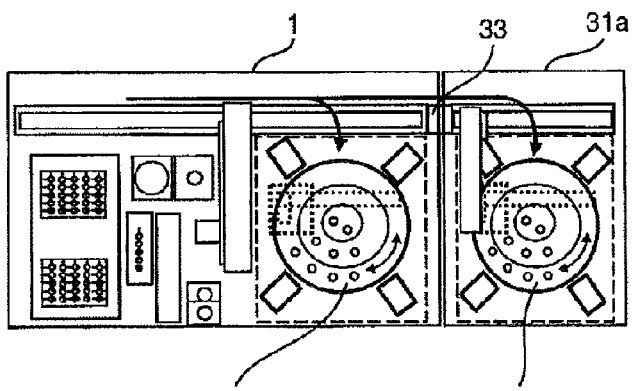
FIG. 18 is a view illustrating a layout of a specimen inlet in the genetic test system according to the present embodiment.

FIG. 18 illustrates not a system configuration in which a heating/cooling means provided in the nucleic acid amplification unit 12 of the genetic test device 1 or additional device 31a performs temperature control for each position of the reaction vessel described in claim 1 but a system configuration in which a heating/cooling means having another configuration.

FIG. 18 illustrates an example in which a plurality of temperature baths each in which a specific temperature is maintained are provided in the nucleic acid amplification unit 12, and a temperature cycle is performed with the reaction vessel 4 transferred between the temperature baths by the gripper arm 34.

As described above, according to the present invention, it is possible to easily achieve wide-ranging functional extension or function enhancement by system extension, thereby allowing an appropriate workflow for individual customer and a system maximizing added value for customers to be easily provided.

INDUSTRIAL APPLICABILITY

The present invention is particularly effective as a systemization technology of the genetic test device using a genetic test method such as the PCR method or LAMP method.

REFERENCE SIGNS LIST 1 genetic test device
4 reaction vessel
9 dispensing tip
13a to 13g detector
14 electrothermal element
15 temperature measurement element
16 thermostat bath
17 gripper arm
20 waste box
31 additional device for amplification detection
31a (first) additional device for amplification detection
31b (second) additional device for amplification detection
31c (third) additional device for amplification detection
32a (first) additional device for nucleic acid extraction
32b (second) additional device for nucleic acid extraction
33 extension means
34 gripper arm (in additional device)

The invention claimed is:

1. A genetic test system, comprising:
a genetic testing device, a first nucleic acid amplification detection unit and one or more second modular nucleic acid amplification detection units, the genetic testing device being coupled to the first nucleic acid amplification detection unit and the one or more second modular nucleic acid amplification detection units,
wherein the genetic testing device comprises:
a first moveable arm moveable across the genetic testing device and the first nucleic acid amplification detection unit;
a dispenser connected to the first moveable arm configured to dispense a sample and a reagent into a reaction vessel of a plurality of reaction vessels thereby forming a reaction solution;
a first gripper connected to the first moveable arm to convey a reaction vessel of the plurality of reaction vessels,
wherein the first nucleic acid amplification detection unit comprises:
a first rotatable disk comprising a plurality of first liquid baths each configured to accommodate a reaction vessel;
a plurality of first temperature measurement elements, each disposed at one liquid bath of the plurality of liquid baths and configured to detect a temperature value of the liquid in a respective liquid bath;
a plurality of first electrothermal elements, each disposed at one liquid bath of the plurality of first liquid baths, configured to raise or lower a temperature of the liquid in a respective liquid bath;
one or more first light emission detectors arranged around the first rotatable disk and configured to irradiate a reaction solution contained in a reaction vessel in one of the first liquid baths with light at a predetermined excitation wavelength value and detect light emitted from the reaction solution at a predetermined fluorescence wavelength value,
wherein each of the one or more second modular nucleic acid amplification detection units comprises:
a second rotatable disk comprising a plurality of second liquid baths each configured to accommodate a reaction vessel;
a plurality of second temperature measurement elements, each disposed at one second liquid bath of the plurality of second liquid baths and configured to detect a temperature value of the liquid in a respective second liquid bath;
a plurality of second electrothermal elements, each disposed at one second liquid bath, configured to raise or lower a temperature of the liquid in a respective second liquid bath;
one or more second light emission detectors arranged around the second rotatable disk configured to irradiate a reaction solution contained in a reaction vessel in one of the second liquid baths with light at a predetermined excitation wavelength value and detect light emitted from the reaction solution at a predetermined fluorescence wavelength value; and
a second moveable arm, different from the first moveable arm, connected to a second gripper to convey a reaction vessel of the plurality of reaction vessels.

2. The genetic test system according to claim 1, wherein each of the first light emission detectors and the second light emission detectors have the same predetermined excitation wavelength value and have the same predetermined fluorescence wavelength value.

3. The genetic test system according to claim 1, wherein each first light emission detector has a first predetermined excitation wavelength value and a first predetermined fluorescence wavelength value,
wherein, each second light emission detector of the one or more second modular nucleic acid amplification detection units has a second predetermined excitation wavelength value and a second predetermined fluorescence wavelength value,
wherein the first predetermined excitation wavelength value and the second predetermined excitation wavelength value are different, and
wherein the first predetermined fluorescence wavelength value and the second predetermined fluorescence wavelength value are different.

4. The genetic test system according to claim 1, wherein the one or more first light emission detectors includes at least two light emission detectors and the one or more second light emission detectors includes at least two light emission detectors,
wherein among the two or more first light emission detectors, one of the two or more first light emission detectors has a first predetermined excitation wavelength value and a first predetermined fluorescence wavelength value, and, another of the two or more first light emission detectors has a second predetermined excitation wavelength value and a second predetermined fluorescence wavelength value, wherein among the two or more second light emission detectors, one of the two or more second light emission detectors has the first predetermined excitation wavelength value and the first predetermined fluorescence wavelength value, and another one of the two or more second light emission detectors has the second predetermined excitation wavelength value and the second predetermined fluorescence wavelength value, wherein the first predetermined excitation wavelength value and the second predetermined excitation wavelength value are different, and wherein the first predetermined fluorescence wavelength value and the second predetermined fluorescence wavelength value are different.

5. The genetic test system according to claim 1, wherein each of the one or more first light emission detectors and each of the one or more second light emission detectors has a different predetermined excitation wavelength value and a different predetermined fluorescence wavelength value.

6. The genetic test system according to claim 1,
wherein the genetic test system includes at least two second modular nucleic acid amplification detection units, and
wherein one of the at least two least two second modular nucleic acid amplification detection units is a nucleic acid extraction device that extracts at least one of DNA and RNA from a sample.

7. The genetic test system according to claim 3,
wherein at least two second modular nucleic acid amplification detection units are coupled to the genetic testing device,
wherein each second light emission detector of the another one of the one or more second modular nucleic acid amplification detection units has a third predetermined excitation wavelength value and a third predetermined fluorescence wavelength value,
wherein the first predetermined excitation wavelength value, the second predetermined excitation wavelength value, and the third predetermined excitation wavelength value are different, and
wherein the first predetermined fluorescence wavelength value, the second predetermined fluorescence wavelength value, and the third predetermined fluorescence wavelength value are different.

* * * * *